United States Patent
Guenier et al.

(10) Patent No.: US 7,217,241 B2
(45) Date of Patent: May 15, 2007

(54) DEVICE FOR ORTHODONTIC INTERVENTIONS

(75) Inventors: Albert Guenier, Den Haag (NL); Angelo Favonio, Vimercate-Milan (IT)

(73) Assignee: Faro Fabbrica Apparecchiature Razionali Odontoiatriche S.p.A, Ornago-Milan (IT)

( * ) Notice: Subject to any disclaimer, the term of this patent is extended or adjusted under 35 U.S.C. 154(b) by 420 days.

(21) Appl. No.: 10/450,890

(22) PCT Filed: Dec. 19, 2001

(86) PCT No.: PCT/EP01/15039

§ 371 (c)(1),
(2), (4) Date: Nov. 10, 2003

(87) PCT Pub. No.: WO02/49505

PCT Pub. Date: Jun. 27, 2002

(65) Prior Publication Data

US 2004/0077930 A1    Apr. 22, 2004

(30) Foreign Application Priority Data

Dec. 20, 2000    (IT)    .................... MI2000A2756

(51) Int. Cl.
*A61B 1/015*    (2006.01)
*A61B 1/04*    (2006.01)
*A61B 1/06*    (2006.01)
*A61B 1/247*    (2006.01)

(52) U.S. Cl. ............ 600/179; 600/102; 600/158; 600/170; 600/172; 600/175; 600/114; 433/30

(58) Field of Classification Search ........... 600/179, 600/102, 175, 176, 170–172, 158, 129, 136, 600/114; 433/29–31
See application file for complete search history.

(56) References Cited

U.S. PATENT DOCUMENTS

| | | | | | |
|---|---|---|---|---|---|
| 4,858,001 | A | * | 8/1989 | Milbank et al. | 348/66 |
| 5,429,502 | A | * | 7/1995 | Cooper et al. | 433/29 |
| 5,449,290 | A | * | 9/1995 | Reitz | 433/31 |
| 5,702,249 | A | * | 12/1997 | Cooper | 433/29 |
| 5,737,013 | A | * | 4/1998 | Williams et al. | 348/66 |
| 5,836,762 | A | * | 11/1998 | Peithman | 433/29 |
| 5,908,294 | A | * | 6/1999 | Schick et al. | 433/29 |
| 5,961,445 | A | | 10/1999 | Chikama | |
| 6,276,934 | B1 | * | 8/2001 | Rakocz | 433/29 |
| 6,398,549 | B1 | * | 6/2002 | Koivisto et al. | 433/29 |
| 2002/0103420 | A1 | * | 8/2002 | Coleman et al. | 600/173 |
| 2003/0100817 | A1 | * | 5/2003 | Wang et al. | 600/102 |

* cited by examiner

*Primary Examiner*—John P. Leubecker
(74) *Attorney, Agent, or Firm*—Hedman & Costigan PC; James V. Costigan

(57) ABSTRACT

A direct view rigid video-endoscope (11) supported by an articulated and compensated arm (2), equipped with a grip (3) crossed by an air flow (92) originating from a generator (93) upstream of the device. The air flow (92) comes out of small holes (8) made in the distal end (28) of the grip (3), at the base of an optical tube (10).

12 Claims, 12 Drawing Sheets fig 3 fig 4 fig 6 fig 11

DEVICE FOR ORTHODONTIC INTERVENTIONS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION (1) Field of the Invention

The present invention refers to dentistry and in particular to orthodontic intervention tools in which the main element consists of a direct view rigid video-endoscope installed on an articulated and compensated arm. Such a device is intended mainly but not exclusively for orthodontic interventions, and allows the dental surgeon to work under control using a video screen and carries out the functions of an intra-oral and extra-oral video camera, of a directable lighted mirror, of a transilluminator, of a negatoscope, of a saliva-removing pump, and in some cases advantageously replaces the polymerizing lamp and the shadow-free operating lamp.

(2) Description of Related Art

With video cameras for the oral cavity of the prior art the greatest difficulties for the dental surgeon who works with the video-screen control derive, on the one hand from the difficulty in synchronizing one's owns movements with the image on the screen and on the other hand the difficulty in focusing the image itself on the tooth upon which he intervenes.

It must be kept in mind that to work in comfort on a tooth only looking at the image transmitted on the control video its necessary on the one hand that the image of the tooth on the screen is directed in the same way as what the dentist usually sees, with or without his hand-held mirror, in the mouth of the patient, on the other hand that the image of the tooth sits in a fixed position on the screen, and only the image of the tool moved by the dentist must have the possibility of moving round the tooth to end up with the image of the point upon which the intervention must take place.

To get to the point upon which the intervention must take place the dentist must therefore move the image-taking aperture of the video-endoscope so that the image of the field of vision on the control video-screen simultaneously comprises the part of tooth to be treated and the image of the distal end of the work tool which he holds, without the image of the tool blocking that of the point to be reached on the tooth to be treated.

Moreover, the current state of the art does not allow images of the distal faces of teeth—in other words those furthest from the image-taking point—to be taken with a direct view rigid video-endoscope, at the base of the oral cavity of the patient, this is not currently possible due to the size of rigid video-endoscopes available on the market. It is therefore necessary to apply to deviated view rigid video-endoscopes according to the known art.

On the video-endoscope according to the present invention deviated vision is obtained with a tube sleeve which completely surrounds the optical tube and can rotate with respect to it.

When the dental-surgeon manoeuvres a deviated vision video-endoscope to move the image-taking aperture in order to look for the best imaging angle to work on a tooth, the angle made by the plane of the CCD, the abbreviation commonly used to indicate a charge-coupled device, of the video-endoscope with the plane of the field of vision continually changes which has the consequence, on the control screen, of modifying the addressing of the images of the tooth observed and of making the dentist lose his references, who therefore finds it very difficult to position the image of the end of his tool on the image of the precise point of the tooth which he tries to reach.

Such a change in addressing of the image of the tooth, on the control screen, between two positions of the image-taking aperture is the result of the product of a rotation and of a homotethy, i.e. of a biunique correspondence between segments of superposing planes. Such a homotethy is direct or indirect depending upon the respective relative positions of the distal end of the tool which the dental surgeon is holding, of the tooth having its image taken and of the image-taking aperture of the video-endoscope.

It follows from this that, when the dentist who intervenes on a tooth using video control, he moves—from a given working angle—the image-taking aperture to look for a different angle of view and that if he wishes to continue his work in favourable conditions, he must re-establish the position of the tooth in the direction which it occupied previously. For this, it is necessary that one makes an opposite displacement, in other words the inverse product of the rotation and of the homotethy which modified the position of the image of the tooth passing from the starting position to the end position of the image-taking aperture, to the new image of the tooth which appears on the screen. The device according to the present invention is directed to allow the user to carry out in favourable conditions such a rotation and such a homotethy, direct or inverse, through the combined action of a micromotor which makes the CCD rotate about its axis and of an electronic plate which inverts the addressing of the signals at the level of the CCD, which has the consequence of inverting the images from left to right and from bottom to top. To operate in comfort, moreover, using video control it is necessary that the image-taking aperture is neither misty nor blocked by splashes of water or by solid particles deposited in it. The device according to the invention provides a solution to this problem supplying, at the distal end of the endoscope, on the image-taking aperture, a suitable air flow also when the deviated vision sleeve rotates upon itself.

As outlined above, a further condition must be satisfied to operate in favourable conditions using video control: it is necessary that the image of the visualised object is in a fixed position on the screen. The device according to the invention provides a solution to this problem by associating with the video-endoscope an articulated and compensated arm upon which said video-endoscope is fastened with a pawl.

On the other hand, in the prior art the dental surgeon must face the economic and economic problems posed by the multiplication of tools around the dentist's chair, tools which are, nevertheless, indispensable for carrying out the profession.

BRIEF SUMMARY OF THE INVENTION

The present invention is aimed at the purpose of providing a device of which one of the main elements is a rigid deviated vision video-endoscope, realized so as on the one hand to allow work using video control and on the other hand allowing the examination of the teeth with the method of transillumination and moreover allowing the dentist to use it as:
- a shadow-free operating lamp for more easily illuminating the distal zones of the teeth of the patient, reducing the operating times;
- as a hand-held mirror without misting;
- as a negatoscope, i.e. to read radiographs on the control screen;
- as a polymerising lamp;
- as a surgical suction tube, thus improving the ergonomics of the dental surgery reducing the number of tools around the dentist's chair where the patient sits, improving the working conditions of the dentist and reducing the investments and, therefore, giving to the patient a better quality of care.

DETAILED DESCRIPTION OF THE INVENTION

The device according to the invention is defined, in its essential components, in the first claim whereas its variants and preferred embodiments are specified and defined in the dependent claims. From the following description, the device comprises:

A—a rigid video-endoscope with a directable image-taking device of the CCD type, i.e. of the charge-coupled device type, consisting of an elongated grip with an optical tube. The video-endoscope is connected to a control screen.

B—A tube sleeve which rotates about itself without limitation, capable of sliding on the optical tube and capable of being locked with a pawl at the distal part with respect to the grip of the video-endoscope.
This sleeve is
both deviated by 90° according to a preferential use of the video endoscope for working using the video, for the examination of the tooth with the technique of transillumination, or as a lamp for polymerising the composites in the zones which cannot be directly accessed.
Directed vision is obtained with a total deviation prism fixed at the distal end of the sleeve. Moreover, the directed vision sleeve requires a light source intended to illuminate its field of vision, consisting of one or more lamps housed in its distal end;
and direct, in the extension of the optical tube, with a variant use of the device as an illuminating mirror, as a lamp for polymerising the composites in a direct access zone, or as a tool for radiograph examination on a control screen.

C—An articulated compensated arm.

D—An electronic plate which manages the rotation/inversion of the images top/bottom and left/right.

The rigid video-endoscope consists of a grip to the end of which is fixed an optical tube coaxial with it. The grip contains a CCD catcher coaxial with the optical tube. It is crossed by an air flow originating from a generator upstream from the device. The air flow leaves the grip from small holes made in its distal end, at the base of the optical tube. The optical tube is realised to provide, on the plane of the CCD catcher, an image of the object being examined, the imaging being directed in the extension of the axis of the video-endoscope.

The deviated vision sleeve carries, fixed to its distal end, a 90° transmission device consisting of a total reflection prism and a light source, consisting of one or more lamps housed around the entry face of the prism and with axes perpendicular to said face of the purism so as to illuminate the field of vision.

A variant embodiment or the device according to the invention foresees that the axes of the lamps make an angle B which is not zero so as to concentrate their luminous beams on a predetermined point.

The deviated vision sleeve has the characteristic of sliding on the optical tube and of locking with a pawl to the distal part with respect to the grip of the video-endoscope, remaining free to rotate upon itself without limitation. Moreover, it has the characteristic of having a greater inner diameter than the outer diameter of the optical tube so as to allow an air flow coming out of the air holes, arranged in the distal end of the video-endoscope, to circulate freely in the interstice between said two tubes and to leave near to the distal part of said optical tube. Moreover, it has the characteristic that the exit face of the prism, when the sleeve is locked with the pawl to the grip of the video-endoscope, stays parallel to and in contact with the front lens of the optical tube, and, moreover, that it carries, fixed on its inner face, a coating of a thickness equal to that of the interstice existing between the tube sleeve and the optical tube. This thus allows the two tubes to slide freely, since said coating gasket occupies almost all of the circumference of the sleeve and leaves only a small gap in front of the entry face of the prism to allow the passage of air at this precise point to eliminate misting and sprays which could cover said face of the prism during the dentist's work.

The device carries, at its distal end, moreover, a flat mirror which forms an angle of 30–60° with the optical tube, the nearest part of the mirror being close to the entry face of the prism so that the air flow which keeps the entry face of the prism clean also keeps the surface of the mirror clean.

On the one hand the mirror is also used to move the cheek during the use of the device according to the invention, to work using video control and on the other hand to reflect the light rays originating from the object to be seen directly by the operator in the use of the device as a hand-held mirror by the dentist, without the video screen. In this use, the dentist no longer needs the shadow-free operating lamp since he has a hand-held mirror which does not mist up and which lights up the field of vision.

DESCRIPTION OF THE PREFERRED EMBODIMENT

According to a preferred embodiment, the plane of the end of the lamp is in front of the entry face of the prism. The power supply wires of the lamp pass into the interstice between optical tube and sleeve, at the base of which the clamps are arranged, which, by contact, ensure, when the sleeve rotates upon itself, the connections between two rings arranged inside the grip of the video endoscope, which are themselves connected to an external electrical energy supply.

The tube sleeve is advantageous for carrying out, in advantageous conditions, a rotation on the control video screen of the image of the field of vision, keeping the centre of such a rotation at the centre of the screen. To carry out such a rotation, the operator, with one hand, keeps the tube sleeve in a fixed position and with the other hand, makes the body of the rigid video-endoscope rotate.

According to a variant embodiment the flat mirror is replaced with a concave or convex mirror.

According to a second variant the mirror is fixed to a removable support which locks on the distal wall of the sleeve, in such a way allowing, for hygiene reasons, the mirror to be changed for each patient at a reduced cost.

According to another variant of the device, the light source of the deviated vision sleeve consists of one or more lamps with axes parallel to the axis of the optical tube and which are installed in the distal end of the sleeve and the 90° transmission device consists of a flat mirror associated with a total reflection prism. The deviated vision sleeve of such a variant has the characteristic of carrying, at its distal end, a flat mirror on which a total reflection prism is fixed so that the axis of the exit face of the prism coincides with the axis of the optical tube of the video-endoscope and is parallel to and in contact with the front lens of said optical tube. According to a further variant embodiment, it has, moreover, the characteristic that the distal end of the lamp(s) is arranged in a plane behind the plane of the front lens of the optical tube so that an angular transmission mirror, the plane of which forms an angle of 45° with respect to the axis of the tube for reaching the object, and rotating about an axis coinciding with the axis of the optical tube, can rest upon the edge of the front lens of the optical tube.

Said part of the mirror outside of the prism is used to reflect the rays of light coming from the lamps to illuminate the imaging field and to reflect the rays emitted by the object to be seen directly by the operator, in the use as a hand held-mirror by the dentist, without using the video screen.

The deviated vision sleeve used for the examination of a tooth with the method of transillumination requires, at its distal end, a total reflection mirror to allow a 90° deviated vision; it has the characteristic that it slides on the optical tube with the possibility to rotate upon itself and to lock itself in the distal part of the grip of the video-endoscope, that the flow of light that it emits to illuminate the field of vision is emitted by a source consisting of one or more lamps arranged in the distal end of an articulated arm fixed onto the end of the sleeve; the exit face of the total reflection prism is parallel to the plane of the front lens of the optical tube and comes into contact with said front lens when it is locked with a pawl in the grip of the video-endoscope. The small arm is, moreover, realised in such a way that the flow of light coming out of the lamp(s) is directed towards the entry face of the prism leaving sufficient space between the outlet plane of the light rays and the entry face of the prism for the tooth of the patent. In practice, it is essential that the same sleeve can be used to examine all teeth.

For this reason the small arm must have two degrees of rotation associated with an image inversion so that the transillumination sleeve can be used for any position of the tooth under examination in the oral cavity: upper or lower, left or right dental arch. The device according to the invention provides a solution to this problem. In fact, the end part of the arm consists of a first tube fixed to the distal end of the body of the sleeve, in the opposite direction to the prism entry, the axis of said tube coinciding with the optical entry axis of the prism. The first tube extends with a second coaxial tube having the characteristic of being capable of rotating upon itself and of being curved by 360° so that its distal face is opposite the entry face of the prism leaving, however, sufficient space for a tooth between the two faces.

The second tube is, moreover, characterised in that its distal end carries one or more lamps whose light rays are directed to the entry face of the prism. The feeding lines of such lamps pass inside said tubes, and therefore inside the sleeve at the base of which they are connected to the clamps which, by contact, ensure, when the sleeve rotates upon itself, the connections to an external electrical energy supply.

According to a preferred embodiment, the video-endoscope is locked with a pawl on a support fixed to the distal end of a compensated articulated arm which allows it to be kept stably in position when the arm is left by the operator. The compensated part of the arm is mobile in a vertical plane and, in its distal end, supports a third tube which is free to rotate upon itself about a vertical axis, according to a conventional technique, whatever position the compensated part is in.

The part nearest to the compensated part stays in a horizontal plane whereas the distal end has the possibility of moving, in a vertical plane, from bottom to top. The characteristic part of the compensated arm lies in the fact that it rotates in its right angled distal part and in the fact that it extends in a fourth coaxial cylindrical tube which is free to rotate upon itself and carrying, at its distal end, a ball-bearing the axis of which is perpendicular to the axis of said tube inside which the grip of the video-endoscope becomes locked, the axes of the bearing and of the video-endoscope coinciding. The fourth tube contains, moreover, a small motor, with a transmission axis which is also coaxial with said tube, which carries at its end a worm screw, which makes the inner part of the ball bearing rotate in a plane perpendicular to the axis of the motor thus taking the video-endoscope with it which is integral therewith.

The top/bottom and left/right image inversions are managed by a dual-control electronic plate: one control for the top/bottom inversion and one control for the left/right inversion. The electronic plate carries out the command for the top/bottom inversion by inversion of the addressing of the video signals emitted by the CCD catcher; on the other hand, it carries out the left/right inversion command first by commanding the small motor installed inside the fourth tube to make a half-turn and then carrying out the inversion of the addressing of the video signals emitted by the CCD catcher.

BRIEF DESCRIPTION OF THE SEVERAL VIEWS OF DRAWINGS

For the purpose of illustrating the particularities and the advantages of the invention some of its typical embodiments are shown here, as examples and not for limiting purposes. In particular.

From FIGS. 1 to 15 the following is noted.

Figure 2:
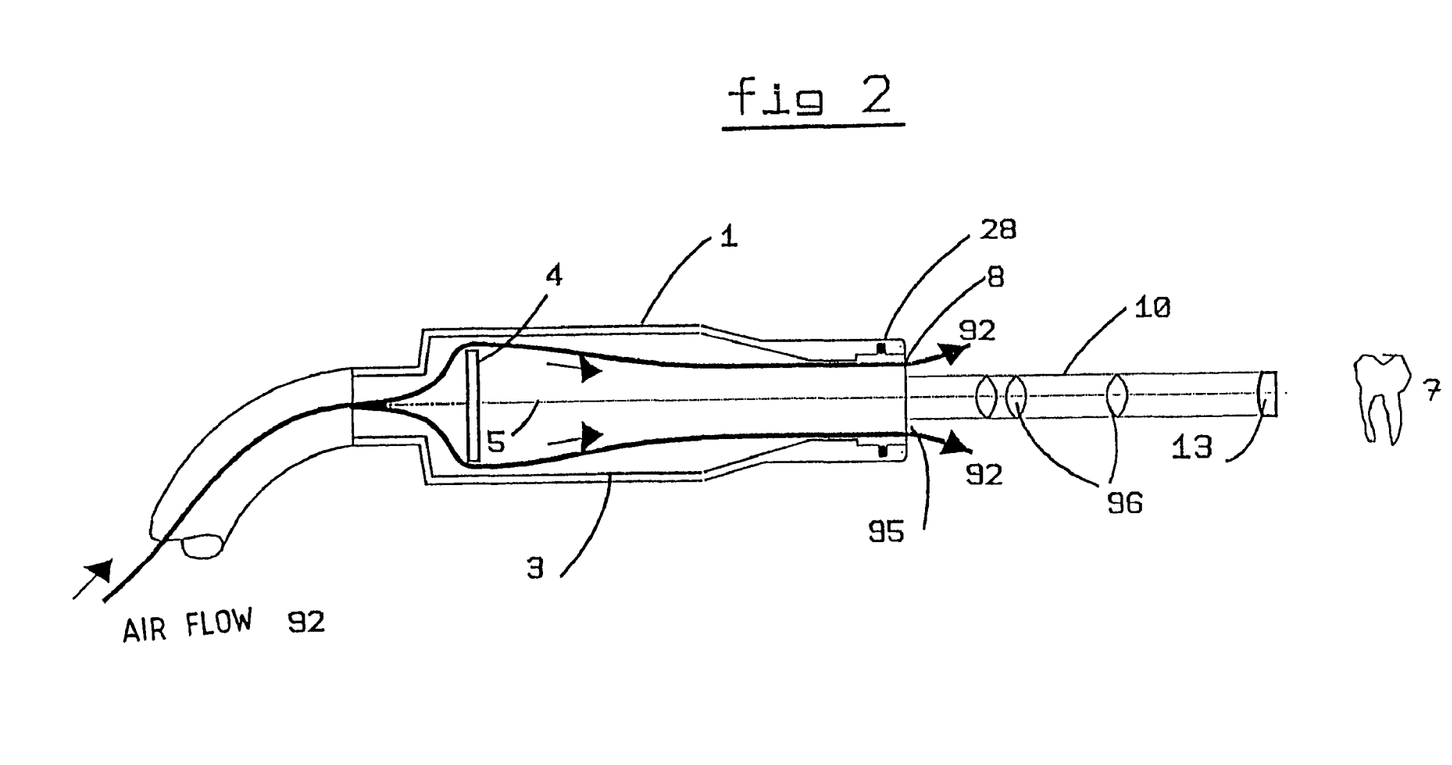
FIG. 2 illustrates a longitudinal section view of the direct view rigid video-endoscope 1.

The direct view rigid video-endoscope 1 with the image-taking device for accumulating signals with the CCD catcher 4 comprises a grip 3 which extends in an optical tube 10 coaxial with it. The grip 3 also contains the CCD catcher 4 which is coaxial with the optical tube 10.

The optical tube 10 is realised to provide, on the plane of the catcher 4, an image of the object examined 7, for example a tooth. The imaging is directed towards the extension of the axis 5 of the video-endoscope 1. The video screen to which the video-endoscope 1 is connected is not shown in the drawings. The video-endoscope 1 has the characteristic that its grip is crossed by an air flow 92 coming from a generator 93 upstream of the device. The air flow 92 leaves the grip via small holes 8 made in its distal end 28, at the base of the optical tube 10. In a variant embodiment already quoted above the grip 3 also contains a micromotor to make the CCD catcher 4 rotate about its axis for the inversion of the images.

Figure 3:
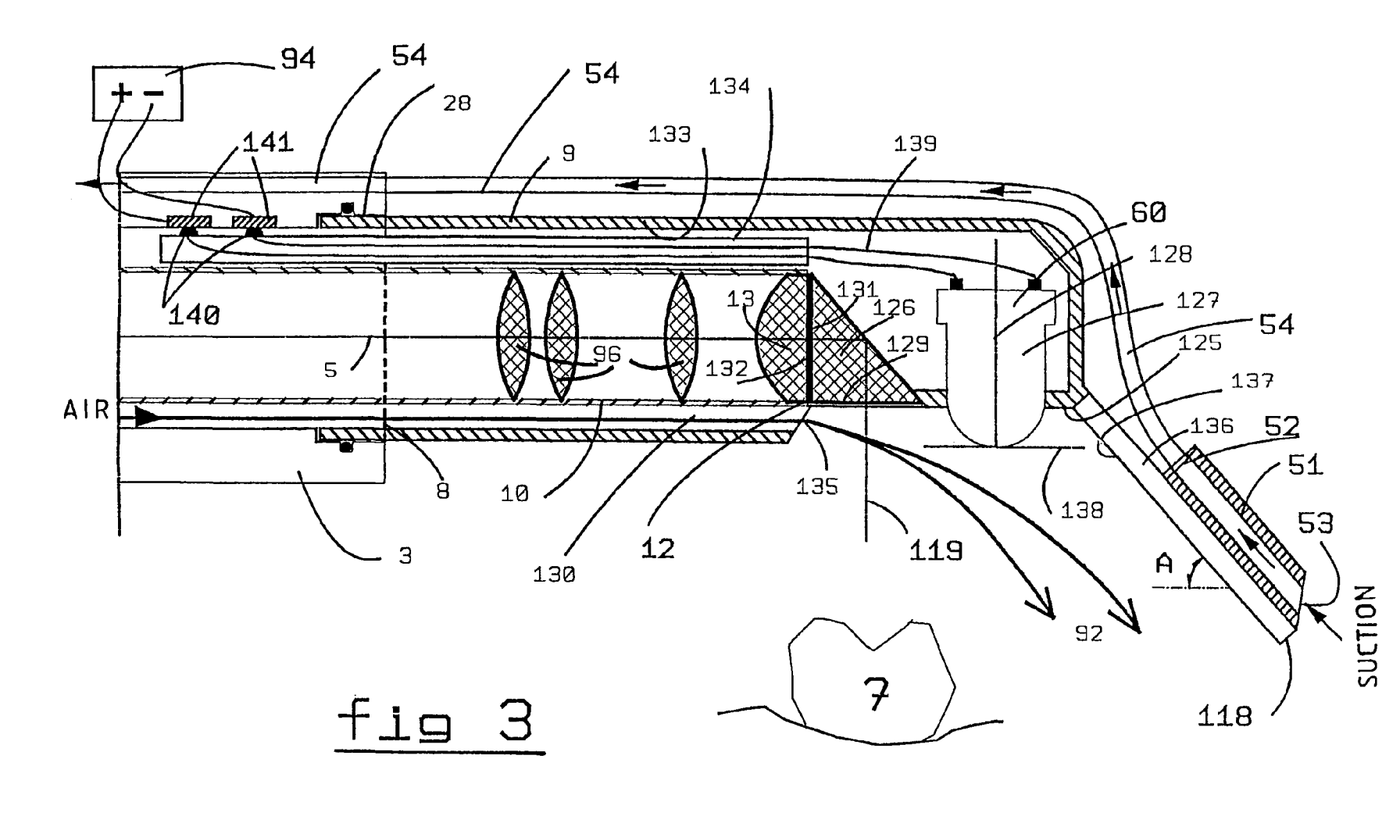
FIG. 3 illustrates a longitudinal section view of the sleeve 9.

The mobile sleeve (9) covers the optical tube 10 intended to obtain a view deviated by 90° and to illuminate the field of vision 7, in the use of the device to work in the oral cavity using video control. The inner diameter of the mobile sleeve (9) is greater than the outer diameter of the optical tube (10) so as to allow, in the interstice (130) between the sleeve (9) and the optical tube (10) the circulation of an air flow (92).

The sleeve 9 is coaxial with the optical tube 10 and the 90° transmission device of the sleeve 9 is realised with the total reflection prism 126 installed at its distal end 125; the axis of the exit face 131 of the prism 126 coinciding with the axis 5 of the optical tube 10 and the light source 60 consisting of lamps 127 arranged around the entry face 129 of the prism.126, with axes of the lamps perpendicular to said face 129.

The deviated vision tube sleeve 9 is capable of sliding on the optical tube 10 and of locking with a stop at the distal Part 28 with respect to the grip 3 of the video-endoscope 1, and is free to rotate upon itself without limitation. Its inner diameter is greater than the outer diameter of the optical tube 10 so as to allow an air flow 92 coming out of the air holes, arranged in the distal end 28 of the video-endoscope. The exit face 131 of the prism 126 is parallel to and in contact with the distal face 132 of the front lens 13 of the optical tube 10, and, moreover, the sleeve 9 requires, fixed on its inner face 133, a coating 134 of a thickness equal to that of the interstice existing between the tube sleeve 9 and the optical tube 10. This coating only leaves a small gap 135 opposite the entry face 129 of the prism 126 to allow the air flow 92. The sleeve 9, moreover, carried at its distal end 125 a flat mirror 136, the plane of which—i.e., more generally, its tangent surface—is perpendicular to the plane formed by the optical entry axis 5 of the prism 126 and the optical outlet axis 119 of the prism 126 and which forms an angle A between 30 and 60° with said axis 5 of the optical tube 10. The nearest part 137 of the mirror 136 is close to the entry face 129 of the prism 126 so that the air flow 92, which keeps the entry face 129 of the prism clean, also keeps the surface of the mirror 136 clean.

The mirror 136 carries, on its face opposite the reflection one, an attachment system 51 in the part 52, on which the dentist's surgical suction tube, also not represented, is removably attached, and of which the distal part 53 extends up to the distal part of the mirror 136.

The power supply wires 139 of the lamps 127 are embedded in the gasket or coating 134, at the base of which two clamps 140 are arranged, which, by contact, ensure, when the sleeve 9 rotates upon itself, the connection between two rings 141 arranged inside the grip 3 of the video-endoscope 1, which are themselves connected with an external electrical energy supply 94 for feeding the device. The plane 138 of the ends of the lamps 127 is further forward than the entry surface of the prism 129. Tis feature allows the encumbrance of the head 90 of the sleeve 9, intended to enter into the mouth of the patient, to be reduced.

The tube sleeve 9 is useful for comfortably carrying out a rotation on the control video screen of the image of the field of vision, keeping the centre of such a rotation at the centre of the screen.

To carry out such a rotation, the operator holds the sleeve 9 still with one hand and with the other hand rotates the body of the video-endoscope 1.

The mirror 136 is used to move the cheek of the patient and as a hand-held mirror by the dentist: the light rays coming from the object to be seen directly by the operator without the video screen. As already stated, the mirror 136 can be flat, or else concave or convex.

Figure 4:
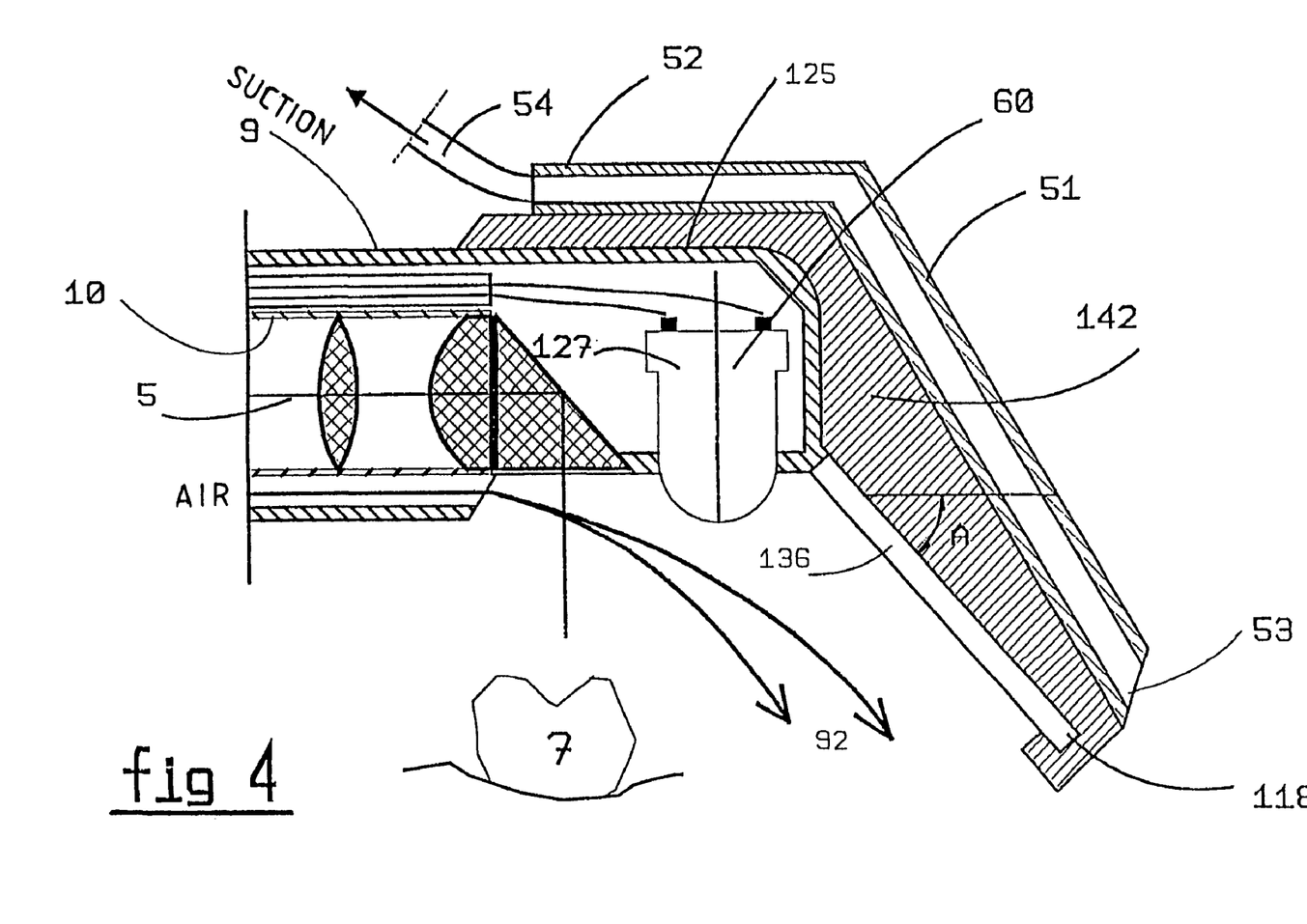
FIG. 4 illustrates a longitudinal section view of the direct view rigid video-endoscope 1 of a variant with a removable mirror

As illustrated in the embodiment of FIG. 4, according to a variant the mirror 136 is fixed to a removable support 142 which locks on the distal part 125 of the sleeve 9, thus allowing, for hygiene reasons, the mirror to be changed after every patient at a lower cost.

Figure 5:
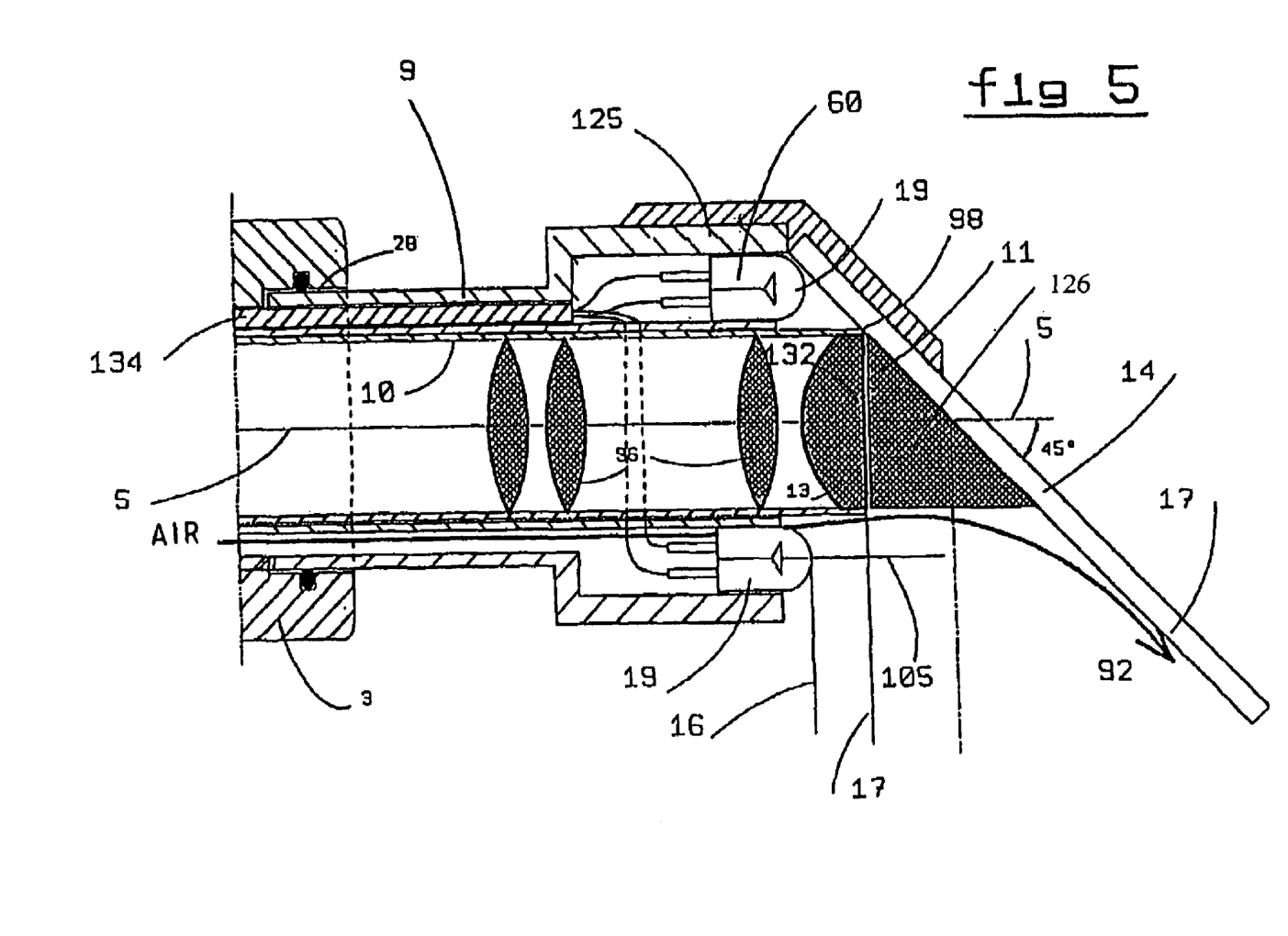
FIG. 5 illustrates a longitudinal section view of a variant of the direct view rigid video-endoscope 1 with a mirror coupled with a deviator prism.

According to another variant of the device, shown in FIG. 5, the light source 60 of the tube sleeve consists of one or more lamps 19 with axes 15 parallel to the axis 5 of the optical tube 10. They are installed in the distal end 125 of the sleeve 9, which carries a 90° transmission device consisting of a flat mirror 14 which makes an angle of 45° with the axis 5 of the optical tube 10 upon which a total reflection prism 6 is fixed so that the axis 5 of the exit face 11 of the prism 6 coincides with the axis 15 of the optical tube 10 of the video-endoscope 1 and is parallel to and in contact with the plane 132 of the front lens 13 of said optical tube 10. According to a further variant shown in FIG. 5, the plane 16 of the distal end(s) of the lamp(s) 19 is further back with respect to the plane 132 of the front lens 13 so that a flat mirror, the plane of which forms an angle of 45° with respect to the axis 5 of the optical tube 10, can abut onto the edge 98 of the front lens 13 of the optical tube 10. The function of the staggering of the planes 16 and 132 is essential for avoiding that the light rays coming from the lamps penetrate into the optical tube 10 and cause interference reflections which without staggering alter the quality of the image on the video-endoscope. According to a further variant shown in FIG. 10, the axis (axes) 128 of the lamp(s) 127 form an angle less than 90° with the optical axis 119 of the entry face 129 of the prism 126.

Figure 6:
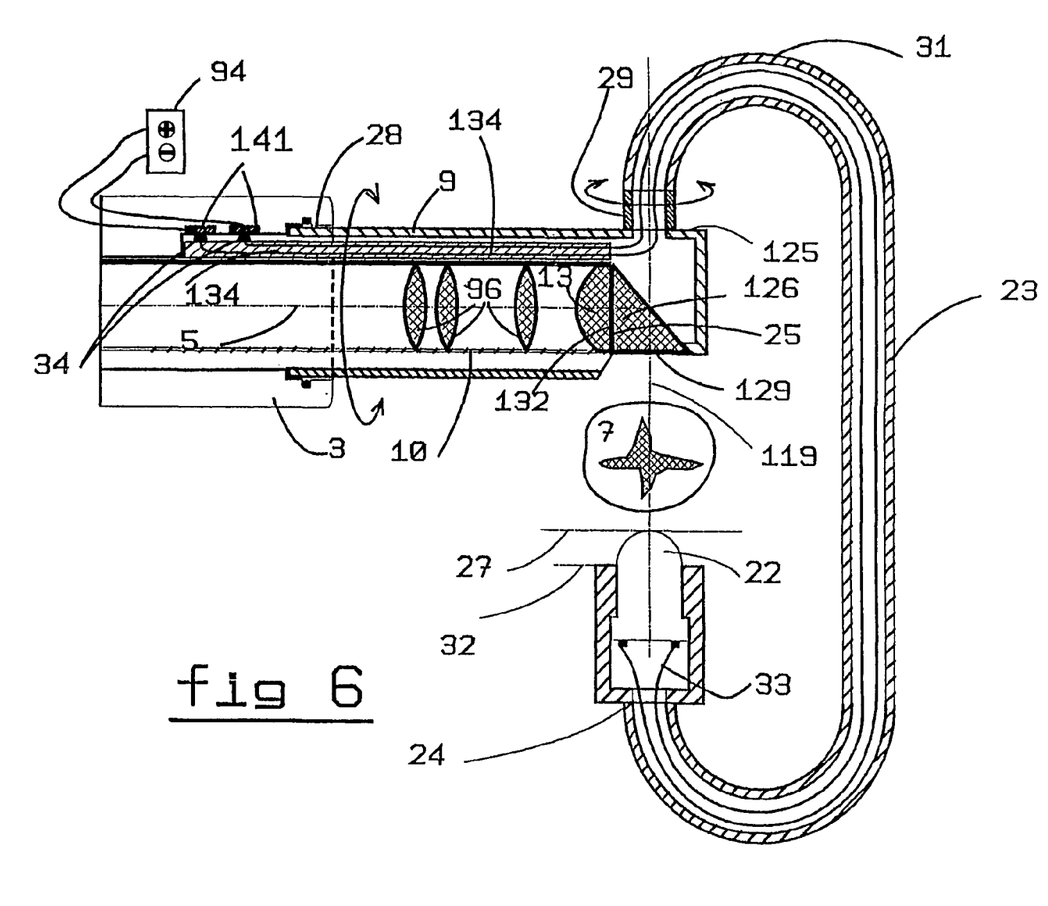
FIG. 6 illustrates a longitudinal section of a variant of the rigid video-endoscope 1 with transillumination.
Figure 7:
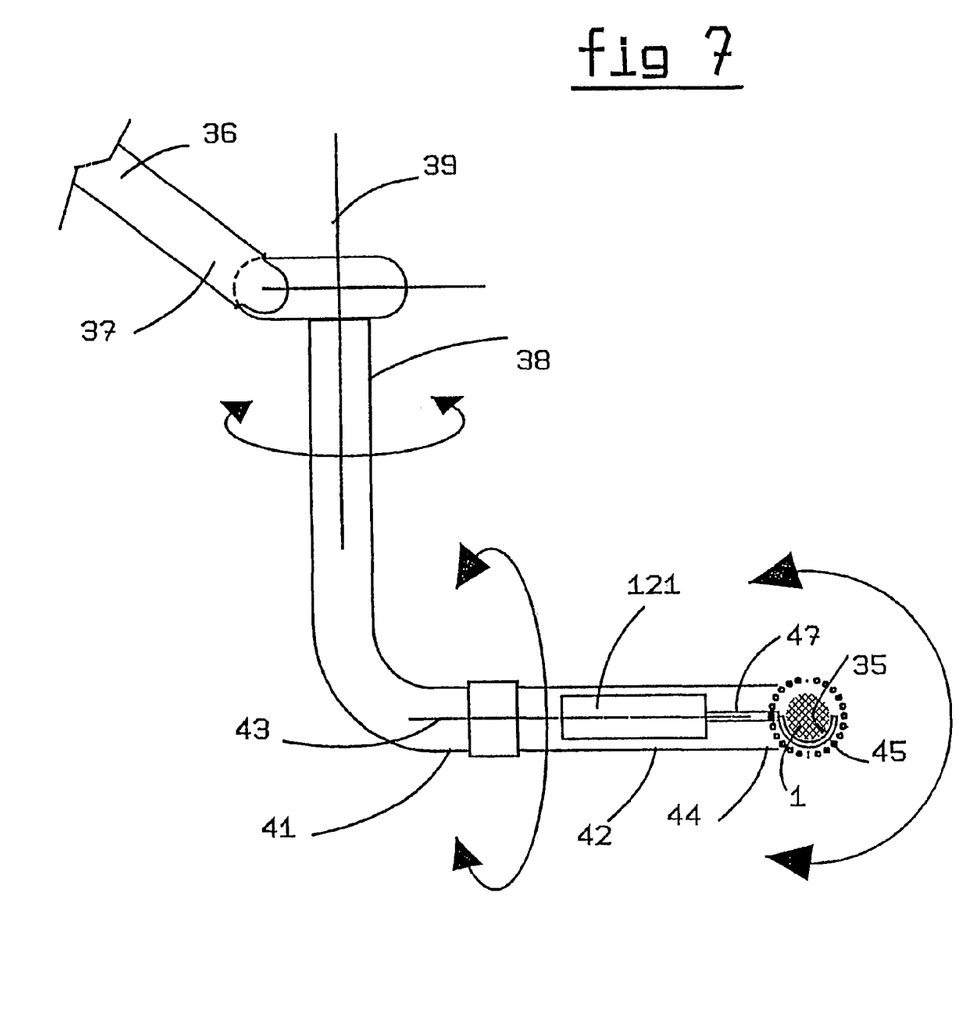
FIG. 7 illustrates a schematic view of the distal part 122 of the compensated arm 2 of the video-endoscope.

As illustrated in the embodiment of FIG. 6, as sleeve 9 is used to examine a tooth with the techniques of transillumination, in other words to obtain its images on the control video with illumination from the rear. The sleeve 9 slides on the optical tube 10 and rotates freely upon itself and lock itself in the distal part 28 of the grip 3 of the video-endoscope 1. It carries, in its distal end 125 a 90° transmission device consisting of a total reflection prism 126 of which the axis of the exit face coincides with the axis 5 of the optical tube and said exit face 25 is parallel to and in contact with the plane 132 of the distal face of the lens 13 of the optical tube 10. Morever, on its distal part 125 is fixed a small arm 23 the nearest part of which consists of a tube 29 in a direction opposite to the entry face 26 of the prism 126 the axis of the tube 29 coinciding with the optical axis 5 of the entry face off the second prism 126 The tube 29 extends with a second coaxial tube 31, capable of rotating upon itself and curved by 360°, so that its distal face 32 is opposite the entry face 129 of the prism 126.

The arm 23, at its distal end 24, carries a light source consisting of one or more lamps 22, the light flow of which is directed to the entry face 129 of the prism 126 leaving, however, sufficient space for a tooth 7 between the two faces.

The power supply wires 33 of such lamps pass inside said tubes 29 and 31, and therefore inside the coating 134, at the base of which they are connected to the clamps 34 which, by contact, ensure, when the sleeve 120 rotates upon itself, the connection to two rings 141 attached inside the grip 3 of the video-endoscope 1 connected to an external electrical energy supply 94.

As illustrated in FIGS. 11 to 14, a mobile sleeve 107 capable of sliding on the optical tube 10 and intended to examine radiographs on a control scree, which carries, at its distal end, a rectangular parallelepiped shape chamber 101, centered on the axis of the sleeve of which the opposite face to said distal image-taking end of the video-endoscope consist of an emery translucent wall 102 upon which the radiograph sheet 103 is fixed in 108

Figure 1:
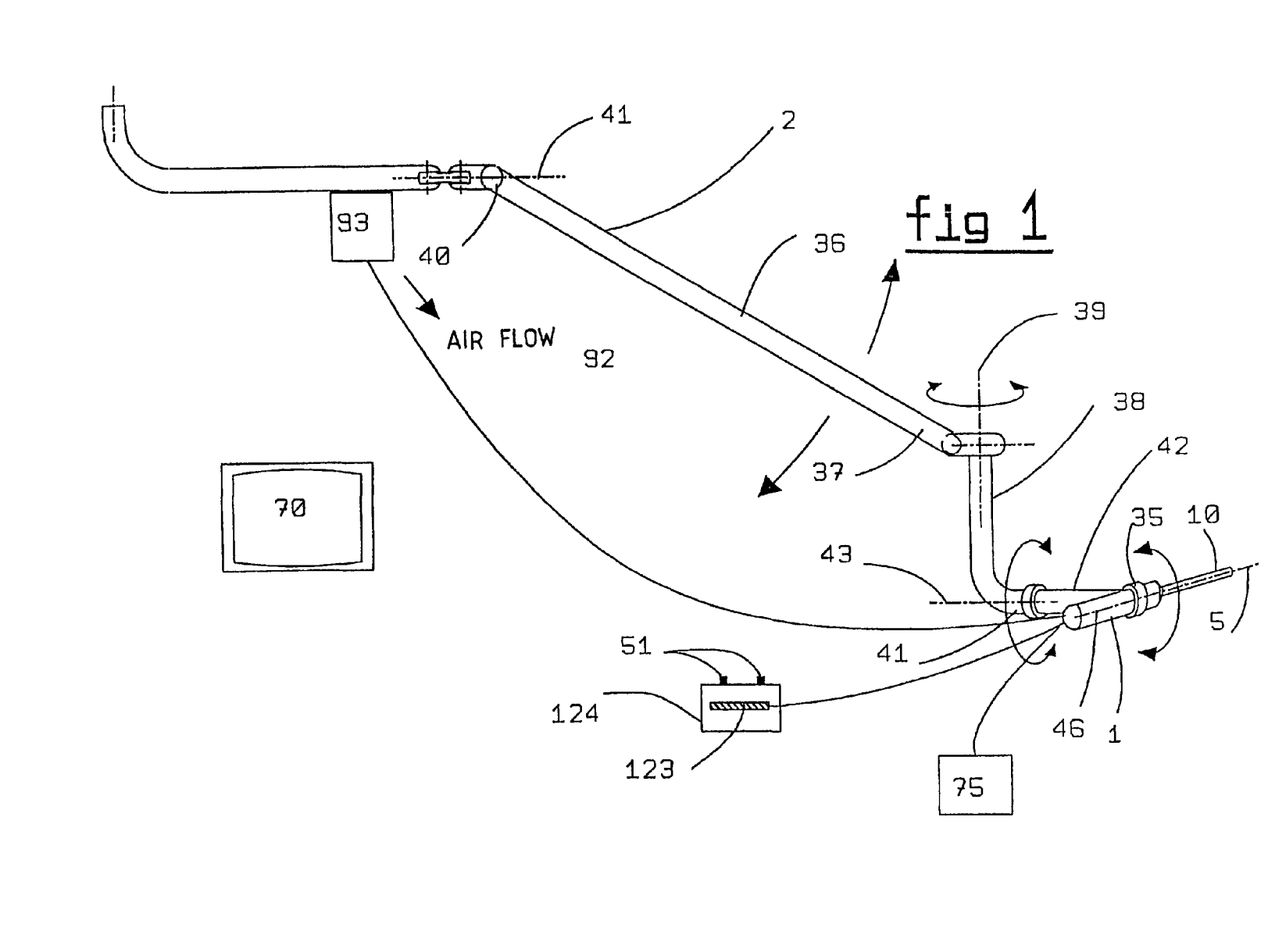
FIG. 1 illustrates the general plan of the device.
Figure 8:
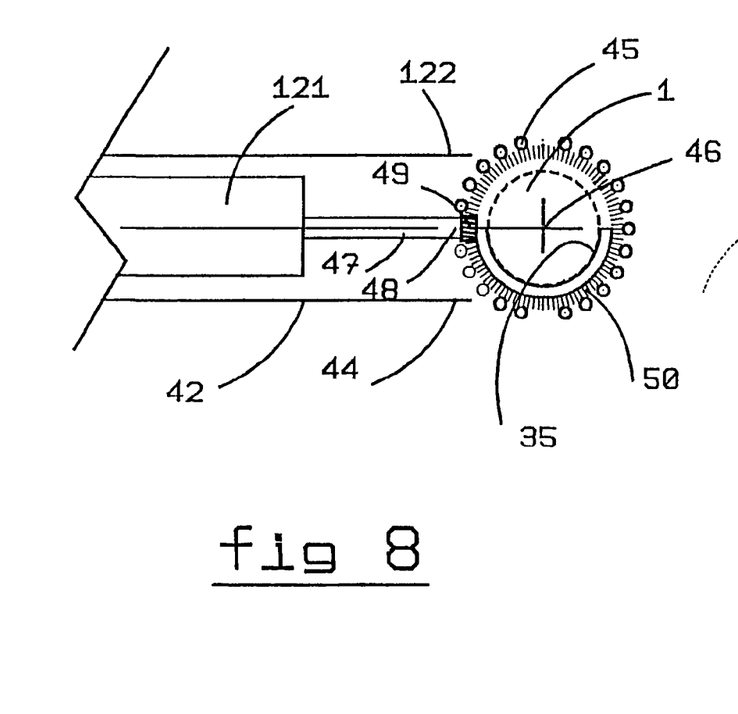
FIG. 8 illustrates a longitudinal section view of the detail of the support 35 of the distal part 122 of the arm 2 of the video-endoscope.
Figure 9:
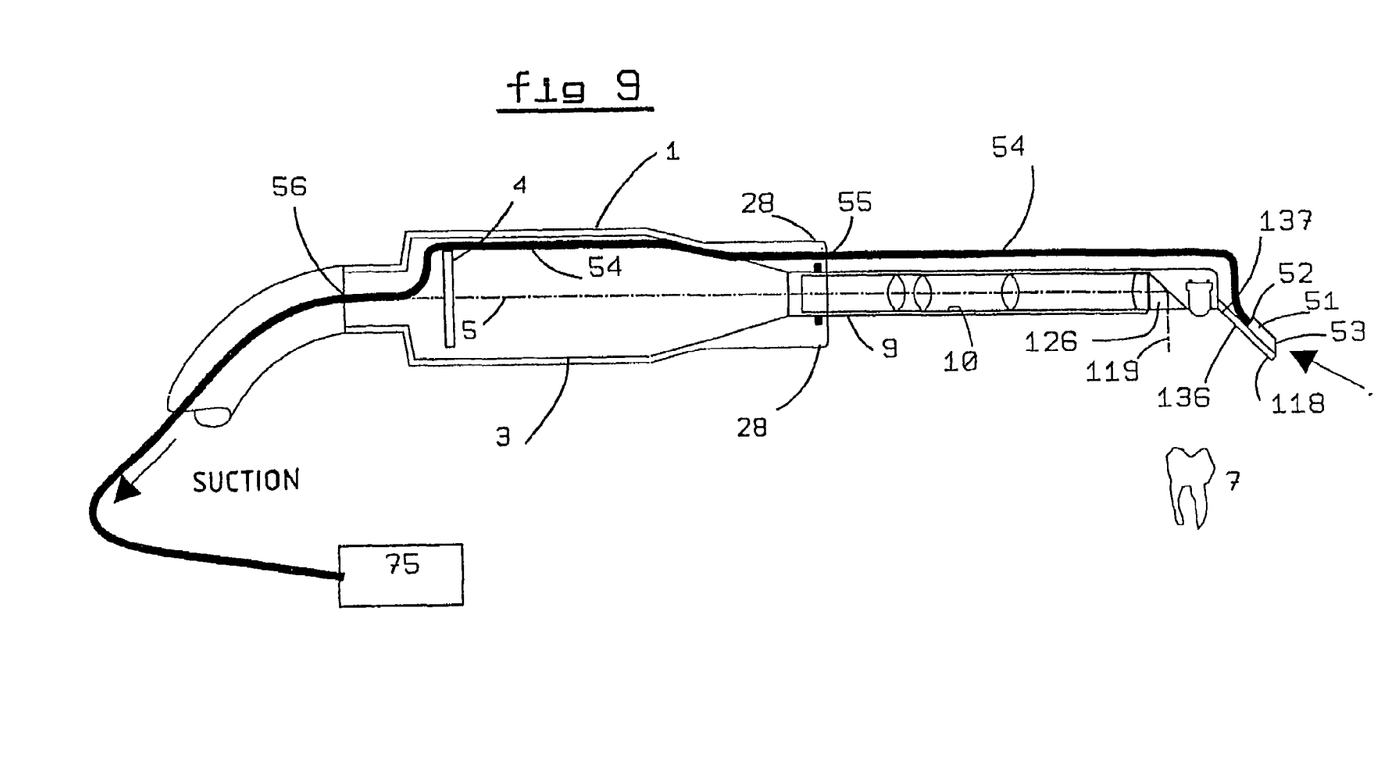
FIG. 9 illustrates a section view of the whole of the embodiment according to the detail of FIG. 4.
Figure 10:
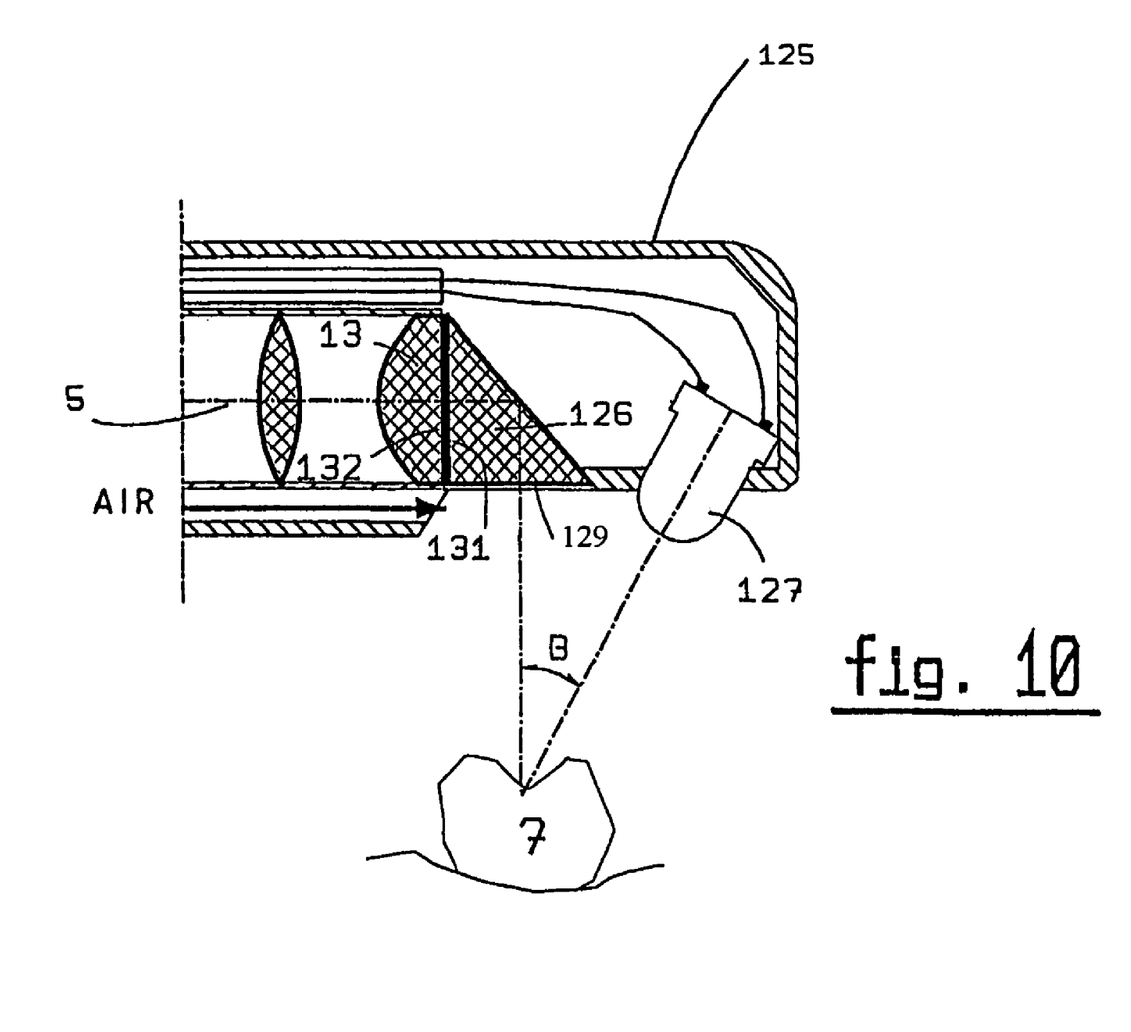
FIG. 10 illustrates a longitudinal section view of the deviated view rigid video-endoscope 1.
Figure 11:
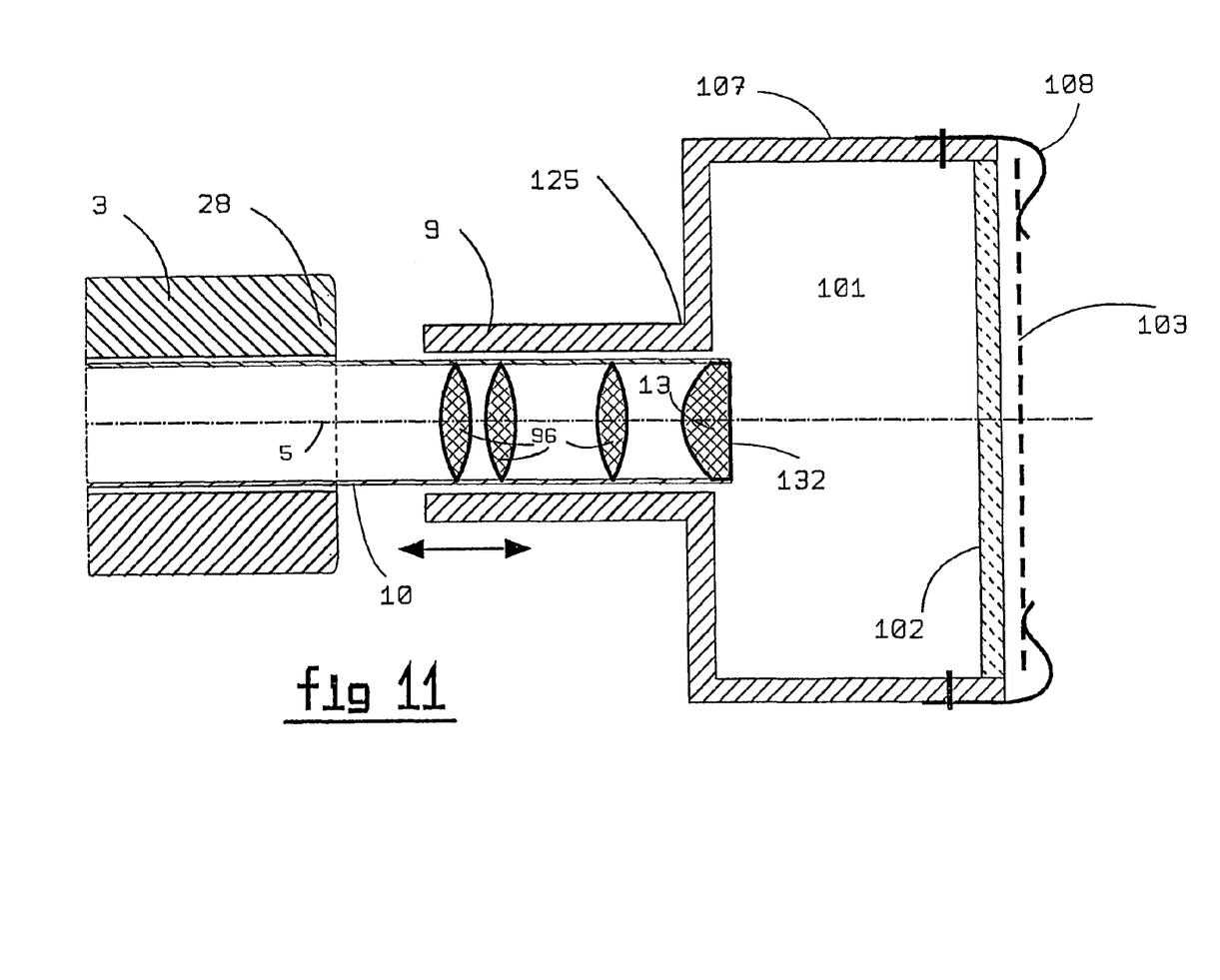
FIG. 11 illustrates a longitudinal section view of the rigid video-endoscope 1 according to the embodiment of FIG. 5 with the tube sleeve intended to be used as a radiograph reader, arranged about the optical tube 10.
Figure 12:
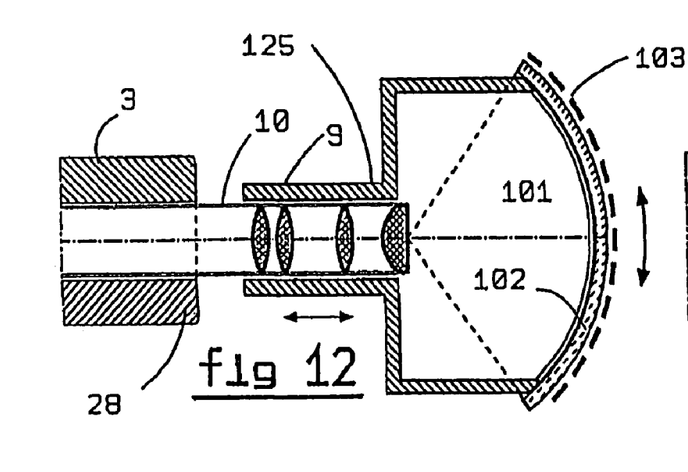
FIGS. 12, 13 and 14 illustrate a longitudinal section view of the rigid video-endoscope 1 according to the design of FIG. 6 with the tube sleeve intended to be used as a radiograph reader, arranged around the optical tube 10.
Figure 13:
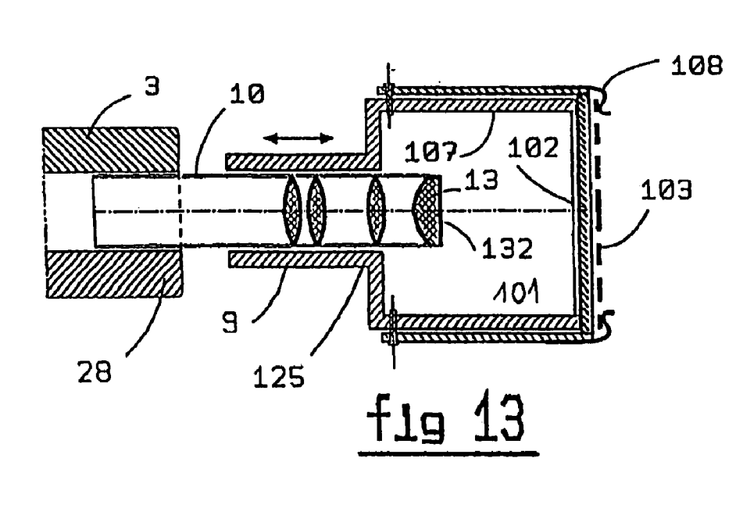
Figure 14:
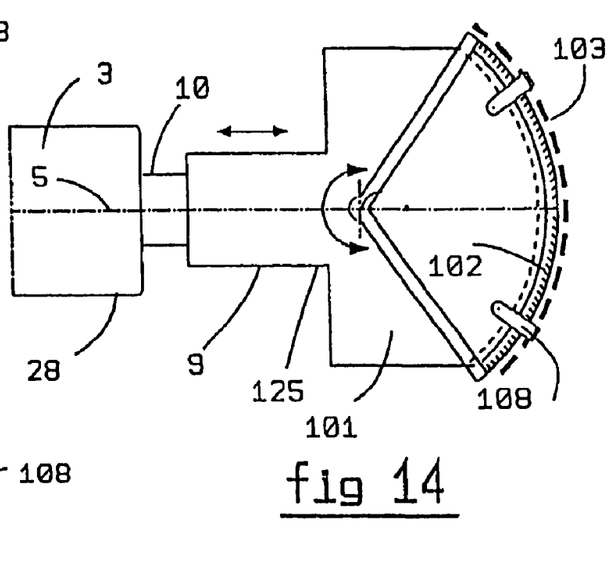
Figure 15:
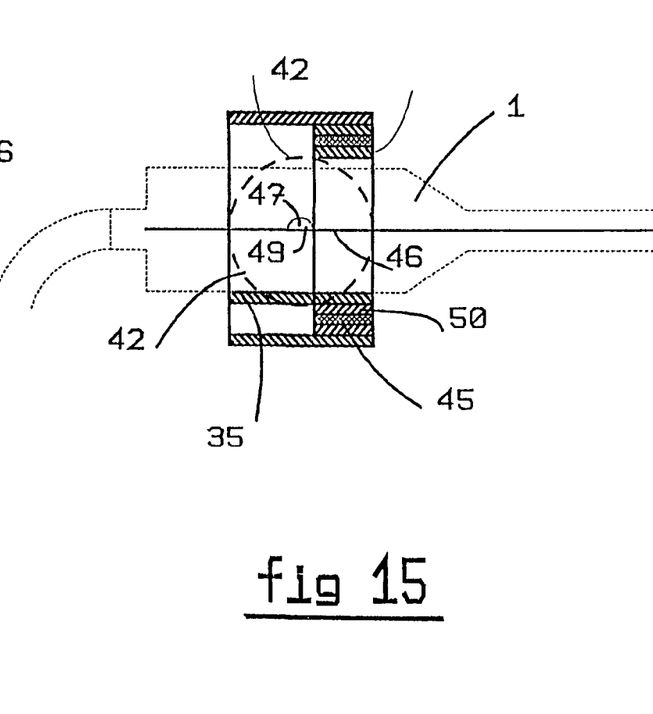
FIG. 15 shows a detail of the compensating bearing of the arm 2 illustrated in FIG. 8.

The compensated articulated arm 2 carries, fixed to its distal end, a support 35—shown in FIGS. 1, 8 and 15—upon which the video-endoscope is locked with the pawl. The compensated part 36 of the arm 2 is mobile in a vertical plane and carries, in its distal end 37, a tube 38 which is free to rotate upon itself about a vertical axis 39 which remains vertical, whatever the position of the compensated part 36. The nearest part 40 of the compensated part 36 constantly remains in thee horizontal plane 41, whereas the distal end 37 has the possibility of moving, in its plane, from bottom to top. The tube 38 rotates in its right-angled distal part 41 and, moreover, extends in a fourth cylindrical tube 42 on the same axis 43, which is free to rotate upon itself and carrying, at its distal end 44, a ball bearing 45, having the axis 46 perpendicular to the axis of said tube 42, inside of which the grip 3 of the video-endoscope 1 locks. The axes 46 and 5 of the bearing and of the video-endoscope 1 coincide. The tube 42 contains a small motor 121, having the transmission axis 47 parallel to the axis 43 of the tube 42 and carries, at its distal end 48, a worm screw 49, which makes the inner part 50 of the ball bearing 45 rotate in a plane perpendicular to the axis 47 of the motor 121, taking the video-endoscope 1 with it which is bound thereto.

An electronic plate 123 arranged in a control box 124, which manages the top/bottom and left/right inversions of the image, carries two buttons 51 for commanding the top/bottom inversion and for commanding the left/right inversion, respectively. The top/bottom inversion command operates the inversion of the addressing of the video signals emitted by the CCD catcher 4; the left/right inversion command first commands the small motor 121 installed inside the tube 42 of the articulated arm 2 to make a half-turn and then inverts the addressing of the video signals emitted by the CCD catcher 4.

The invention claimed is:

1. Device for medical use and particularly for use by a dentist of which the main element is a direct view rigid video-endoscope (1) supported by an articulated and compensated arm (2), comprising:

A—a direct view rigid video-endoscope (1) having a central optical entry axis (5). a signal-accumulating image-taking device with a CCD catcher (4), said endoscope (1) further characterized by a grip (3) possessing a proximal and a distal end (28), an optical tube (10), said optical tube extending into the distal end (28) of said grip (3), said optical tube further being coaxial with said grip (3), said optical tube (10) being realized to provide an image of the object examined (7) on the plane of the CCD catcher (4), the imaging being directed along the central optical entry axis (5) of the video-endoscope (1);

B—a sleeve (9) which is moveable and covers the optical tube (10) and which allows a 90° deviated view to be obtained and a field of view to be illuminated, the sleeve (9) being coaxial with the optical tube (10), a 90° transmission device of the sleeve (9) being realized with a total reflection prism (126) at its distal end (125), the axis of an exit face (131) of the prism (126) coinciding with the axis (5) of the optical tube (10) and a light source (60) consisting of a plurality of lamps (127), said lamps possessing a base portion and a emitter portion and are arranged around an entry face (129) of the prism (126), with axis/es (128) of the lamp/s (127) perpendicular to said entry face (129) of the prism (126);

C—the sleeve (9) capable of sliding on the optical tube (10), capable of rotating freely upon itself and capable of being locked in a distal end (28) of the grip (3) of the video-endoscope (1);

D—a mobile sleeve (107) capable of sliding on the optical tube (10) intended for examining radiographs on a control screen;

E—a compensated articulated arm (2) which carries, fixed at its distal end (122), a support (35) upon which the video-endoscope (1) is locked, a compensated part (36) of the arm (2) being mobile in a vertical plane and carrying, in a distal end (37) a tube (38) free to rotate upon itself about an axis (39), which remains vertical whatever the position of the compensated part (36), a portion (40) of the compensated part (36) remaining constantly in the horizontal plane (41) whereas the distal end (37) is able to move vertically;

F—an electronic plate (123) arranged in a command box (124) equipped with command buttons (51), characterized in that the device comprises a generator (93) adapted to provide an air flow (92) to cross the grip (3) of the endoscope, and the distal end (28) of the grip (3) comprises a plurality of small openings (8) arranged annularly between the distal end of said grip and said optical tube at the base of the optical tube (10) for dispensing the air flow (92).

2. Device according to claim 1, characterized in that the sleeve (9) slides on the optical tube (10), is free to rotate upon itself without limitation and locks with a stop to the distal end (28) of the grip (3) of the video-endoscope (1);

that its inner diameter is greater than the outer diameter of the optical tube (10) so as to allow, in the interstice (130) between the sleeve (9) and the optical tube (10) the circulation of an air flow (92); that the exit face (131) of the prism (126) is parallel to and in contact with the distal face (132) of a front lens (13) of the optical tube (10);

that the sleeve (9) carries, fixed on its inner wall (133), a coating (134) which covers almost the whole of a inner wall (133) of the sleeve (9), leaving only a small passage (135) arranged at the distal end of the coating (134), opposite the entry face (129) of the prism (126) to allow the air flow (92);

that the sleeve (9) carries, at its distal end (125), a mirror (136) the tangent surface of which is perpendicular to the plane formed by the central optical entry axis (5) of the optical tube (10) and an optical outlet axis (119) of the prism (126) and which forms and angle A between 30° and 60° with the central optical entry axis (5) of the optical tube (10); the mirror (136) carries, on a opposite face to a reflecting one, an attachment system consisting of a tube (51) and the distal part (53) of which extends up to the distal part (118) of the mirror (136);

a pair of power supply wires (139) connected to the base portion of the lamps (127) are sunk in a gasket or coating (134), at the base of which two clamps (140) are arranged which, by contact, ensure, when the sleeve (9) rotates upon itself, the connection between two rings (141) arranged inside the grip (3) of the video-endoscope (1).

3. Device according to claims 1 or 2, characterized in that a plane (138) marking the end of the emitter portion of the lamps (127) is further forward than the entry face (129)of the prism (126).

4. Device according to claim 2, characterized in that the mirror (136) is a concave or convex mirror.

5. Device according to claim 2, characterized in that the mirror (136) is fixed to a removable support (142) which locks on the distal part (125) of the sleeve (9).

6. Device according to claim 1, characterized in that with a second sleeve (9) carries, in its distal end (125), a 90° transmission device consisting of a total reflection prism (126) of which the axis of the exit face (25) coincides with the axis (5) of the optical tube (10) and said exit face (25) is parallel to and in contact with the place (132) of the distal face of the lens (13) of the optical tube (10); that the second sleeve (9) has, moreover, a small arm (23) fixed on its distal part (125), the nearest part of which consists of a tube (29) in a direction opposite to the entry face (129) of the prism (126), the axis of the tube (29) coinciding with the optical axis (5) of the entry face (26) of the prism (126); that the tube (29) extends with a second coaxial tube (31), capable of rotating upon itself and curved by 360°, so that its distal face (32) is opposite the entry face (26) of the prism (20); that the arm (23) carries, at its distal end (24), a light source consisting of one or more lamps (22), the light flow of which is directed to the entry face (129) if the prism (126) leaving sufficient space for the tooth (7) of the patient between the two faces.

7. Device according to claim 1, characterized in that the mobile sleeve (107) carries, at its distal end, a rectangular parallelepiped shape chamber, centered on the axis (5) of the sleeve; of which the opposite face to said distal image-taking end of the video-endoscope consists of an emery translucent wall upon which the radiograph sheet is fixed.

8. Device according to claim 1, characterized in that the tube (38) rotates in its right-angled distal part (41); that the distal part (41) extends in a fourth cylindrical tube (42) of the same axis (43), free to rotate upon itself; that at the distal end (44) of the tube (42) a ball bearing (45) is fixed, having an axis (46) perpendicular to the axis of said tube (42), inside of which locks the grip (3) of the video-endoscope (1), the axis (46) and (5) respectively, of the bearing and of the video-endoscope (1) coinciding; that the tube (42) contains a small motor (121), which has its transmission axis (47) parallel to the axis (43) of the tube (42) and which carries, at its distal end (48), a wormscrew (49), which makes the inner part (50) of the ball bearing (45) rotate in a plane perpendicular to the axis (47) of the motor (121), pulling the video-endoscope (1) which it is bound thereto.

9. Device according to claim 8, characterized in that the electronic plate (123) operates the inversion of the addressing of the video signals emitted by the CCD catcher (4) when one of the two buttons (51) of the command box (124) is pressed and when the second command button of the command box (124) is pressed it gives the first order to the small motor (121) installed inside the tube (42) of the articulated arm (2) to make a half-turn, and at the same time inverts the addressing of the video signal emitted by the CCD catcher (4).

10. Device according to claims 1, 2 or 8, characterized in that the grip (3) also contains a micromotor to make CCD catcher (4) rotate about its axis.

11. Device for medical use and particularly for use by a dentist of which the main element is a direct view rigid video-endoscope (1) supported by an articulated and compensated arm (2), comprising:

A—a direct view rigid video-endoscope (1) having with a signal-accumulating image-taking device with a CCD catcher (4), consisting of a grip (3), an optical tube (10), said optical tube extending into said grip (3), said optical tube further being coaxial with said grip (3), said optical tube (10) being realized to provide an image of the object examined (7) on the plane of the CCD catcher (4), the imaging being directed along a central axis (5) of the video-endoscope (1);

B—a sleeve (9) which is moveable and covers the optical tube (10) and which allows a 90° deviated view to be obtained and a field of view to be illuminated, the sleeve (9) being coaxial with the optical tube (10), a 90° transmission device of the sleeve (9) being realized with a total reflection prism (126) at its distal end (125), the axis of an exit face (131) of the prism (126) coinciding with the axis (5) of the optical tube (10)

C—the sleeve (9) being capable of sliding on the optical tube (10), capable of rotating freely upon itself and capable of being locked in a distal part (28) of the grip (3) of the video-endoscope (1);

D—a mobile sleeve(107) capable of sliding on the optical tube (10) intended for examining radiographs on a control screen;

E—a compensated articulated arm (2) which carries, fixed at its distal end (122), a support (35) upon which the video-endoscope (1) is locked, a compensated part (36) of the arm (2) being mobile in a vertical plane and carrying, in a distal end (37) a tube (38) free to rotate upon itself about an axis (39), which remains vertical whatever the position of the compensated part (36), a portion (40) of the compensated part (36) remaining constantly in the horizontal plane (41) whereas the distal end (37) is able to move vertically;

F—an electronic plate (123) arranged in a command box (124) equipped with command buttons (51), characterized in that the device comprises a generator (93) adapted to provide an air flow (92) to cross the grip (3) of the endoscope, and the distal end (28) of the grip (3) comprises a plurality of small openings (8) arranged annularly between the distal end of said grip and said optical tube at the base of the optical tube (10) for dispensing the air flow (92) and in that a light source (60) of the sleeve (9) consists of one or more lamps (19) with axes (105) parallel to the axis (5) of the optical tube (10), being installed in the distal end (125) of the sleeve (9); that the sleeve (9) carries a flat mirror (14) which makes an angle of 45° with the axis (5) of the optical tube (10) upon which a total reflection prism (126) is fixed so that the axis (5) of the exit face (11) of the prism (126) coincides with the axis (5) of the optical tube (10) of the video-endoscope (1) and is parallel to and in contact with the plane (132) of the front lens (13) of said optical tube (10); that the plane (16) of the distal end/s of the lamp/s (19) is further back with respect to the plane (132) of the front lens (13) so that a flat mirror, the plane of which forms an angle 45° with respect to the axis (5) if the optical tube (10), can abut onto the edge (98) of the front lens (13) of the optical tube (10).

12. Device for medical use and particularly for use by a dentist of which the main element is a direct view rigid video-endoscope (1) supported by an articulated and compensated arm (2), comprising:

A—a direct view rigid video-endoscope (1) having a signal-accumulating image-taking device with a CCD catcher (4), consisting of a grip (3), an optical tube (10), said optical tube extending into said grip (3), said optical tube further being coaxial with said grip (3), said optical tube (10) being realized to provide an image of the object examined (7) on the plane of the CCD catcher (4), the imaging being directed along a central axis (5) of the video-endoscope (1);

B—a sleeve (9) which is moveable and covers the optical tube (10) and which allows a 90° deviated view to be obtained and a field of view to be illuminated, the sleeve (9) being coaxial with the optical tube (10), a 90° transmission device of the sleeve (9) being realized with a total reflection prism (126) at its distal end (125), the axis of an exit face (131) of the prism (126) coinciding with the axis (5) of the optical tube (10) and a light source (60) consisting of a plurality of lamps (127), said lamps possessing a base portion and a emitter portion and are arranged around an entry face (129) of the prism (126), with axis/es (128) of the lamp/s (127) perpendicular to said entry face (129) of the prism (126);

C—the sleeve (9) being capable of sliding on the optical tube (10), capable of rotating freely upon itself and capable of being locked in a distal part (28) of the grip (3) of the video-endoscope (1);

D—a mobile sleeve (107) capable of sliding on the optical tube (10) intended for examining radiographs on a control screen;

E—a compensated articulated arm (2) which carries, fixed at its distal end (122), a support (35) upon which the video-endoscope (1) is locked, a compensated part (36) of the arm (2) being mobile in a vertical plane and carrying, in a distal end (37) a tube (38) free to rotate upon itself about an axis (39), which remains vertical whatever the position of the compensated part (36), a portion (40) of the compensated part (36) remaining constantly in the horizontal plane (41) whereas the distal end (37) is able to move vertically;

F—an electronic plate (123) arranged in a command box (124) equipped with command buttons (51), characterized in that the device comprises a generator (93) adapted to provide an air flow (92) to cross the grip (3) of the endoscope, and the distal end (28) of the grip (3) comprises holes a plurality of small openings (8) arranged annularly between the distal end of said grip and said optical tube at the base of the optical tube (10) for dispensing the air flow (92).

* * * * *